(12) United States Patent
Dever et al.

(10) Patent No.: US 8,336,145 B2
(45) Date of Patent: Dec. 25, 2012

(54) DEVICE FOR MITIGATING ODOR IN AN ARTICLE OF CLOTHING OR FOOTWEAR

(75) Inventors: Gerald R. Dever, Cordova, TN (US); Harold A. Howlett, Horn Lake, MS (US); Philip C. Yang, Memphis, TN (US)

(73) Assignee: MSD Consumer Care, Inc., Memphis, TN (US)

( * ) Notice: Subject to any disclaimer, the term of this patent is extended or adjusted under 35 U.S.C. 154(b) by 1234 days.

(21) Appl. No.: 11/961,588

(22) Filed: Dec. 20, 2007

(65) Prior Publication Data

US 2008/0210770 A1    Sep. 4, 2008

Related U.S. Application Data

(60) Provisional application No. 60/876,934, filed on Dec. 21, 2006.

(51) Int. Cl.
*A43D 3/00* (2006.01)

(52) U.S. Cl. .................. 12/128 B; 239/1; 239/36

(58) Field of Classification Search ............ 36/136; 12/128 B; 239/1, 36, 55, 59; 424/76.1
See application file for complete search history.

(56) References Cited

U.S. PATENT DOCUMENTS

| | | | |
|---|---|---|---|
| 1,228,775 A | 6/1917 | Hill | |
| 1,318,939 A | 10/1919 | Willert | |
| 1,601,258 A | 6/1925 | Pajer | |
| 2,072,432 A | 4/1934 | Solomon | |
| 2,025,657 A | 9/1935 | Ganz | |
| 2,086,631 A | 4/1936 | Munro | |
| 2,121,604 A * | 6/1938 | Semke et al. | 36/44 |
| 2,383,960 A | 2/1944 | Dupuy | |
| 2,500,896 A | 3/1948 | Drake | |
| 2,460,405 A | 2/1949 | Abrams et al. | |
| 2,620,228 A | 3/1950 | Howard et al. | |
| 2,642,310 A | 3/1950 | Meek et al. | |
| 2,510,315 A * | 6/1950 | Malberg | 12/117.4 |
| 2,615,754 A * | 10/1952 | Lindenberg | 239/36 |
| 2,626,833 A * | 1/1953 | Valentine | 239/56 |
| 2,780,029 A | 4/1955 | Anthony | |
| 2,765,194 A | 5/1955 | Will | |
| 3,131,036 A * | 4/1964 | Hirschberg | 34/95.1 |
| 3,229,867 A | 1/1966 | Torii et al. | |
| 3,633,538 A | 1/1972 | Hoeflin | |
| 3,772,722 A * | 11/1973 | Gellert | 12/115.8 |
| 3,784,102 A * | 1/1974 | Stults | 239/36 |
| 4,096,975 A | 6/1978 | Furukawa | |

(Continued)

FOREIGN PATENT DOCUMENTS

WO    WO 00/74820 A    12/2000

OTHER PUBLICATIONS

International Search Report (PCT/US 2007/026201) for FC06599 mail date Jun. 16, 2008, 2 pages.

(Continued)

*Primary Examiner* — Marie Patterson
(74) *Attorney, Agent, or Firm* — Dianne Pecoraro; Catherine D. Fitch

(57) ABSTRACT

A deodorizer in particular, a deodorizer substrate with a porous carrier material formed in a monolithic form, and an odor neutralizing composition in the porous carrier material.

9 Claims, 13 Drawing Sheets

U.S. PATENT DOCUMENTS

| | | | |
|---|---|---|---|
| 4,096,994 A | 6/1978 | Bryson | |
| D255,047 S | 5/1980 | Muller et al. | |
| 4,258,004 A | 3/1981 | Valenzona et al. | |
| 4,301,949 A | 11/1981 | Palson et al. | |
| 4,306,679 A | 12/1981 | Dusek et al. | |
| 4,815,659 A | 3/1989 | Turko et al. | |
| 4,944,455 A | 7/1990 | Haust et al. | |
| 4,959,208 A | 9/1990 | Chakrabarti et al. | |
| 4,995,556 A | 2/1991 | Arnold, III | |
| 5,230,115 A * | 7/1993 | Hollister et al. | 12/128 B |
| 5,265,749 A | 11/1993 | Zutler | |
| D345,788 S | 4/1994 | Green | |
| D350,192 S | 8/1994 | Patel et al. | |
| 5,367,735 A * | 11/1994 | Mosier et al. | 12/128 B |
| 5,388,714 A | 2/1995 | Zutler | |
| 5,732,485 A * | 3/1998 | Laughlin et al. | 36/136 |
| D399,945 S | 10/1998 | Bonomo et al. | |
| 5,876,678 A | 3/1999 | Harrell et al. | |
| 5,950,323 A * | 9/1999 | Wroth et al. | 34/104 |
| 5,976,460 A * | 11/1999 | Bourson et al. | 422/5 |
| 6,227,458 B1 * | 5/2001 | Dever et al. | 239/36 |
| 6,237,538 B1 | 5/2001 | Tsengas | |
| 6,244,518 B1 | 6/2001 | Pogue | |
| 6,340,120 B1 | 1/2002 | Seymour | |
| 6,382,406 B1 | 5/2002 | Corbasson | |
| 6,495,097 B1 | 12/2002 | Streit et al. | |
| 6,880,765 B2 | 4/2005 | Tuomikoski et al. | |
| 7,059,540 B2 * | 6/2006 | King et al. | 239/302 |
| 7,261,742 B2 * | 8/2007 | Leskowicz | 8/137 |
| 7,407,922 B2 * | 8/2008 | Leskowicz | 510/278 |
| 2003/0064009 A1 | 4/2003 | Baaset | |
| 2003/0066901 A1 | 4/2003 | Tuttobene, Jr. | |
| 2003/0080197 A1 | 5/2003 | Tuomikoski et al. | |
| 2003/0091465 A1 * | 5/2003 | Hendricks | 422/5 |
| 2005/0148479 A1 | 7/2005 | Barthel et al. | |
| 2005/0205685 A1 | 9/2005 | Jones | |
| 2006/0051312 A1 * | 3/2006 | Kim et al. | 424/76.1 |
| 2006/0051430 A1 * | 3/2006 | Arata et al. | 424/618 |
| 2006/0165622 A1 * | 7/2006 | Hiramoto et al. | 424/65 |

OTHER PUBLICATIONS

U.S. Appl. No. 11/547,142, filed Feb. 6, 1923, Baush.
www.caraselledirect.com/category/
php?Shoe+and+Sneaker+Freshener+balls, Apr. 3, 2006.
www.ckb.en.alibaba.com/products/50067835/50309269/Fine_
chemical/Blue_Block/shoimg.html, Apr. 3, 2006.
www.ttnet.net/search-bin/show_thml.jsp?cartno=-209.190.199.
6015032Au&oday=2006/04/04&prdh . . . , Apr. 3, 2006.
www.tennisgifts.com/sneaker_ball.htm, Apr. 7, 2006.

* cited by examiner

DEVICE FOR MITIGATING ODOR IN AN ARTICLE OF CLOTHING OR FOOTWEAR

This application claims priority under 35 U.S.C. 119(e) to U.S. Provisional Patent Application Ser. No. 60/876,934 titled "Device for Mitigating Odor in an Article of Clothing or Footwear", filed on Dec. 21, 2006. The entire contents of said application is incorporated herein by reference thereto.

FIELD OF THE INVENTION

Some example embodiments of the present invention are generally directed to a deodorizer, and in particular, to a deodorizer substrate with a porous carrier material formed in a monolithic form, and an odor neutralizing composition in the porous carrier material.

BACKGROUND

Malodors are usually caused by chemicals that are perceived at very low concentrations. Although malodors may not necessarily be dangerous to health at low levels, they can affect one's enjoyment of the environment. Among those malodors, shoe/foot odor is a common problem in people's daily life.

Conventional deodorizers include powders and sprays. Deodorant powders use a variety of ingredients such as inorganic compounds of aluminum, zinc, and zirconium to provide a desired effect. However, powders and sprays can cause a mess and it is almost impossible to apply the powder or spray into some locations, such as the foot portion of high boots or a high top sneakers.

Other conventional deodorizes include shoe insoles or patches.

Usually relatively high loading of fragrance containing perfumes (i.e. about 10 milligrams (mg) or greater) may be used in the compositions of the insoles or spray, to provide sufficient "odor masking" by diffusing fragrance into the environment to mask the malodors. Such concentrated loadings of fragrance in the perfume component can be expensive and cause the adhesive holding the deodorizer to the footwear to soften, causing the deodorizer to loosen from the footwear.

SUMMARY

It would be desirable to provide a convenient and economic deodorizer, in which the effective component could be easily applied to and removed from the shoe interior without a mess, and provide sufficient odor masking and odor neutralizing at the same time. It would be her desirable to provide such a deodorizer that had both an effective deodorization capability and a long shelf life.

One example embodiment of the present invention is an odor deodorizer. The odor deodorizer may include a disk-shaped porous carrier material of microporous high density polyethylene, having pores in the range of 45-100 microns; an odor neutralizing composition of undecylenic acid and/or a derivative thereof in the porous carrier material; and a disk-shaped talc filled, injection-moldable polypropylene housing sized to fit in a shoe and having a plurality of holes and containing the porous carrier, the housing being movable between an open to a closed configuration.

A second example embodiment of the present invention is a shoe deodorizer. The shoe deodorizer may include a porous carrier material formed in a monolithic form without a casing and sized to insert in a shoe; and an odor neutralizing composition in the porous carrier material. Optionally, the carrier material may be a porous polyalkylene material. The polyalkylene material may be polyethylene or microporous high density polyethylene. Optionally, the pore size of the carrier material is up to about 100 microns in arithmetic average, and more preferably from about 45 microns to about 90 microns in arithmetic average. In some instances of the second example embodiment, the shoe deodorizer eliminates up to 90% of shoe odor. Optionally, the odor neutralizing composition further includes undecylenic acid and/or a derivative thereof, and at least one of fragrances or flavor agents. Optionally, the undecylenic acid derivatives are methyl ester and ethyl ester undecylenic derivatives, wherein the ratio of methyl ester undecylenic derivative to ethyl ester undecylenic derivative is from about 5/95 to about 30/70 by weight. Optionally, the amount of undecylenic acid and or a derivative thereof is from about 5% to about 50% by weight of the odor neutralizing composition. Optionally, the shoe deodorizer substrate is formed into a shape of a shoe tree or a shell of a shoe tree, or a disk. Optionally, the shoe deodorizer, particularly when formed as a shoe tree, may farther include a mechanical part operably coupled to the shoe deodorizer substrate and configured to hold the shoe deodorizer substrate in a shoe, which optionally may be a flexible rod extending from the shoe deodorizer substrate.

A third example embodiment of the present invention is an odor deodorizer. The odor deodorizer may include a porous carrier material; an odor neutralizing composition in the porous carrier material; and a housing containing a plurality of holes, the housing containing the porous carrier. Optionally, the housing is molded from materials with minimal tendency to absorb the odor neutralizer and or fragrance. The material of the housing may optionally be a plastic material, for example a talc filled, injection-molded polypropylene material. Optionally, the housing may have at least one sheath configured to cover at least a subset of the plurality of holes. The sheath may optionally be movably connected to the housing and movable from a closed position to an open position. Optionally, the number and size of the holes may be chosen to eliminate at least 80% and preferably at least 90% of malodor in 8 hours. Optionally, the number of holes may be up to 50, and more preferably up to 42. Optionally the holes may be up to 3.0 mm in diameter, and more preferably up to 2.0 mm in diameter. The size and number of holes may be chosen to provide at least 20, and preferably at least 30 uses of the deodorizer, where optionally each use comprises an approximately 8 hour exposure of the odor to the deodorizer.

A fourth example embodiment of the present invention is an article of manufacture. The article of manufacture may include a shoe deodorizer substrate containing an effective amount of an undecylenic acid and or a derivative thereof in a porous monolithic carrier; and a sealed package formed at least in pan of a heat sealing, low organic vapor transport packaging film, the package containing the shoe deodorizer substrate. The article may optionally be configured so that it loses less than 5% of the odor neutralizing composition in one month aging at 50° C. and less than 5% of the odor neutralizing composition in three months aging at 40° C., wherein the aging takes place with the shoe deodorizer substrate contained within the sealed package. Optionally the article may have a shelf life of the of about 1 year to up to 2 years. Optionally, the sealed package may further include a sealed inner layer of polyethylene terephthalate located inside the packaging film and surrounding the shoe deodorizer substrate. Optionally, the article may have no expiration date.

A fifth example embodiment of the present invention is a method for preparing a shoe deodorizer. The method may include providing an odor neutralizing premix composition comprising an effective amount of an undecylenic acid and or a derivative thereof; forming a porous carrier material into a shape; applying the premix to the formed shaped carrier material; and allowing the release of an effective amount of the odor neutralizing composition from the carrier material. Optionally, the premix is a liquid formulation. Optionally, premix is applied into the formed shaped carrier material via absorption.

Further areas of applicability of the present invention will become apparent from the detailed description of some example embodiments provided hereinafter. It should be understood that the detailed description and specific examples, while describing some example preferred embodiments of the invention, are intended for purposes of illustration only and are not intended to limit the scope of the invention.

BRIEF DESCRIPTION OF THE DRAWINGS

The present invention will become more fully understood from the detailed description of example embodiments and the accompanying drawings, wherein.

DETAILED DESCRIPTION OF EXAMPLE EMBODIMENTS

Figure 1:
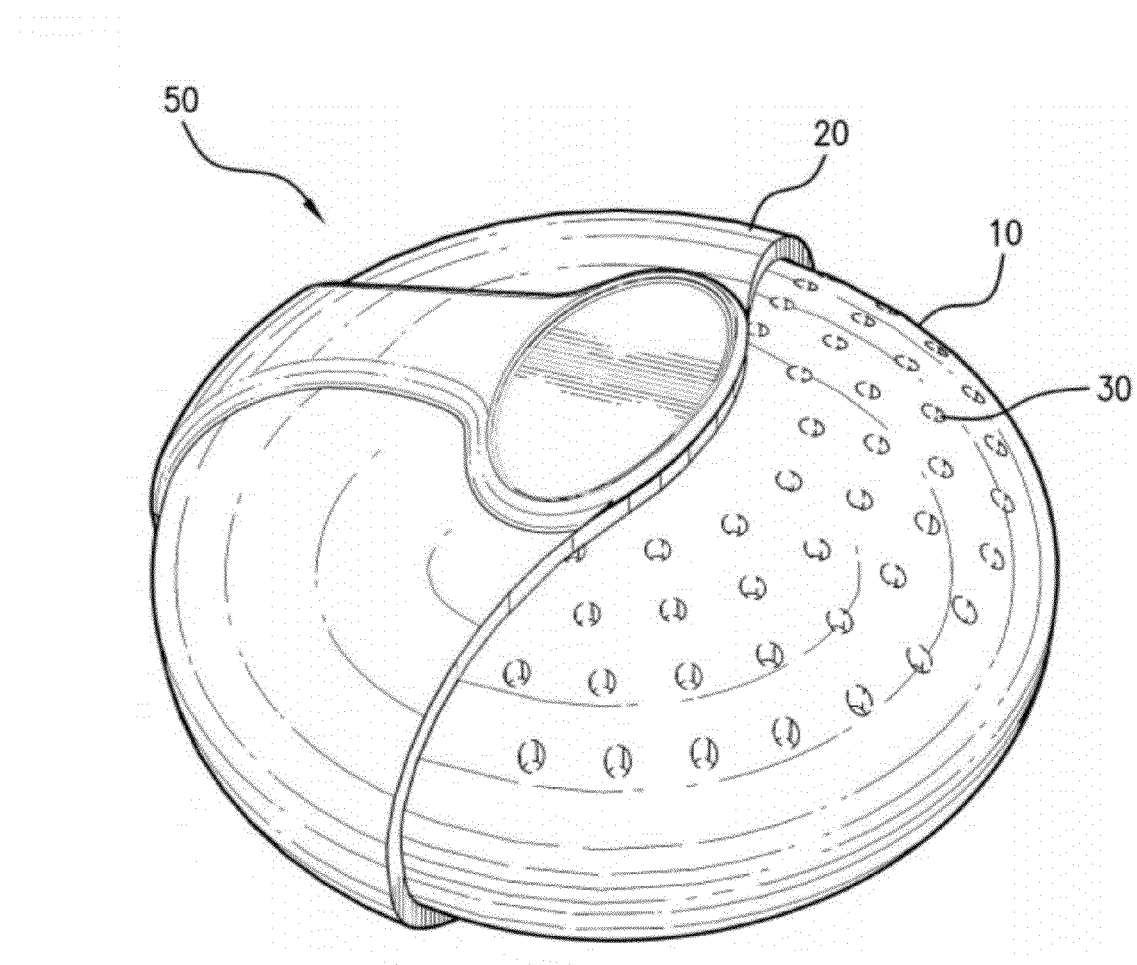
FIG. 1 is a perspective view of one example of a deodorizer, according to an example embodiment of this invention.

The following description of some example embodiment is merely exemplary in nature and is in no way intended to limit the invention, its application, or uses.

Some example embodiments of the present invention provide deodorizers with dual mechanism of "odor neutralizing" (reducing or eliminating the vaporization of the malodors by diffusing molecules which complex with the malodor molecules in the shoe) and "odor masking" (diffusing fragrance into the environment) at the same time. Other example embodiments of the present invention provide deodorizers with the odor neutralizing mechanism only.

Specifically, one example embodiment provides a shoe deodorizer substrate comprising a porous carrier material, formed in a monolithic form without a casing and sized to insert in a shoe; and an odor neutralizing composition in the porous carrier material. An alternative example embodiment provides an odor deodorizer comprising a porous carrier material; an odor neutralizing composition in the porous carrier material; and a housing containing a plurality of holes. The neutralizing compositions of these example embodiments may diffuse out of the porous structure of the carrier material without requiring any moving or ratable parts to initiate the odor neutralizing action, although the example embodiment with the housing may be alternatively opened and closed.

The term "shoe" is used herein to mean any product for the foot to which the deodorizer can be inserted or attached, such as shoes, sneakers, insoles, arch supports, athletic footwear, sandals and the like.

The term "undecylenic acid" is used herein to mean any of several isomeric straight-chain unsaturated acids $C_{11}H_{20}O_2$ (as undecylenic acid). "Undecylenic acid" is the common name of 10-undecenoic acid ($CH_2$=$CH(CH_2)_8COOH$), which is an organic unsaturated fatty acid derived from cracking natural castor oil under pressure. Undecylenic acid is used in the manufacture of pharmaceuticals, cosmetics and perfumery including anti-dandruff shampoos, anti-microbial powders and as a musk in perfumes and aromas.

Undecylenic acid is a natural fungicide and is FDA approved in over-the-counter medications for skin disorders or problems. It is the active ingredient in medications for skin infections, and relieves itching, burning, and irritation. For example, it is used against fungal skin infections such as athlete's foot, ringworm, *Candida albicans*. It is also used in the treatment of psoriasis. Undecylenic acid is also proven to have anti-bacterial and anti-viral properties that are effective on viral skin infections such as the herpes simplex virus.

U.S. Pat. No. 6,495,097 discloses a composition and a method for using a undecylenic composition to neutralize or reduce malodors and bad taste. U.S. Pat. No. 5,182,103 discloses undecylenic acid, among many other compounds, to be useful in combination with an aluminometasilicate coated composite to provide an improved deodorant for refrigerators, garbage cans, automobiles, leather insole for shoes, paper diapers, menstrual products and general in-room use. U.S. Pat. No. 4,517,919 discloses the use of undecylenic acid as deodorant in a flexible absorbent pad for use in several products, including animal litter boxes.

The term "odor neutralizing composition" refers to a composition with odor neutralizing properties which may also include other components, e.g., a fragrance composition, or a flavor composition, or a combination thereof.

As used herein, "Pore" means one of many small openings in the carrier material.

As used herein, "hole" means a hollowed-out place in the housing of a deodorizer.

The term "high-density polyethylene" (HDPE) is used herein to mean a polyethylene thermoplastic, typically made from petroleum or other hydrocarbon. HDPE has little branching, giving it stronger intermolecular forces and tensile strength than lower density polyethylene. HDPE is harder and more opaque and can withstand somewhat higher temperatures (120° C. for short periods, 110° C. continuously). High-density polyethylene, unlike polypropylene, cannot withstand normally required autoclaving conditions.

The term "talc" is used herein to mean a mineral composed of hydrated magnesium silicate with the chemical formula $H_2Mg_3(SiO_3)_4$ or $Mg_3Si_4O_{10}(OH)_2$.

Figure 2:
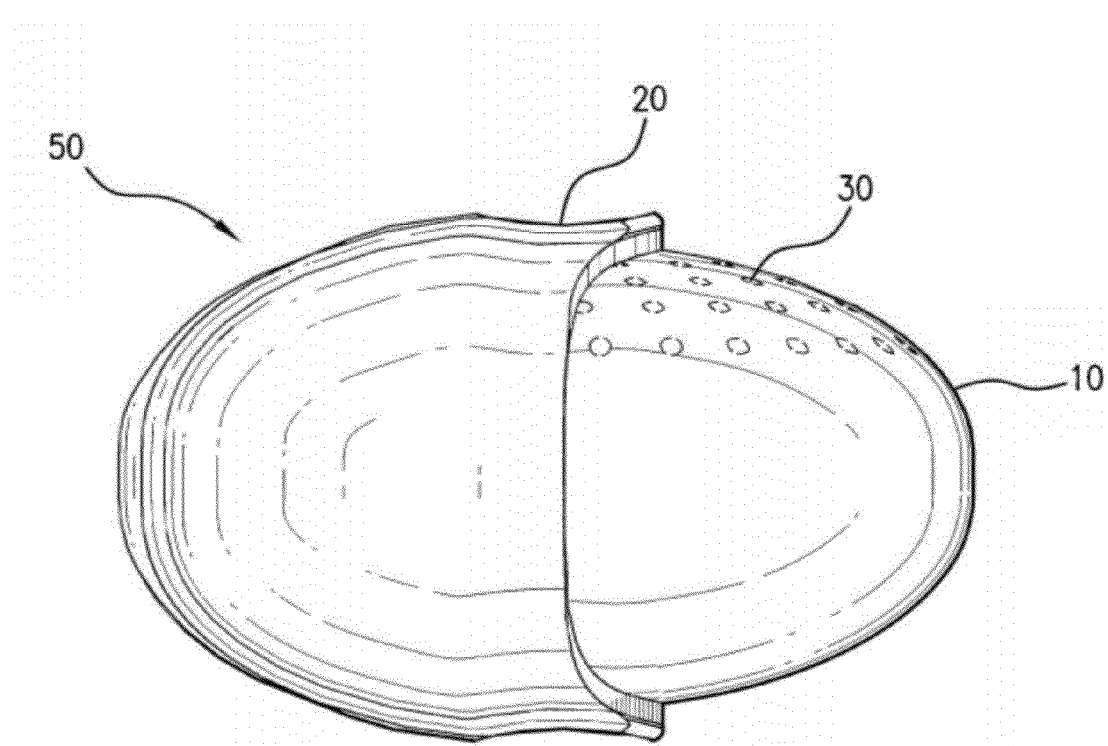
FIG. 2 is a side view of the example deodorizer according to an example embodiment of this invention, showing the holes of the housing in its open position.
Figure 3:
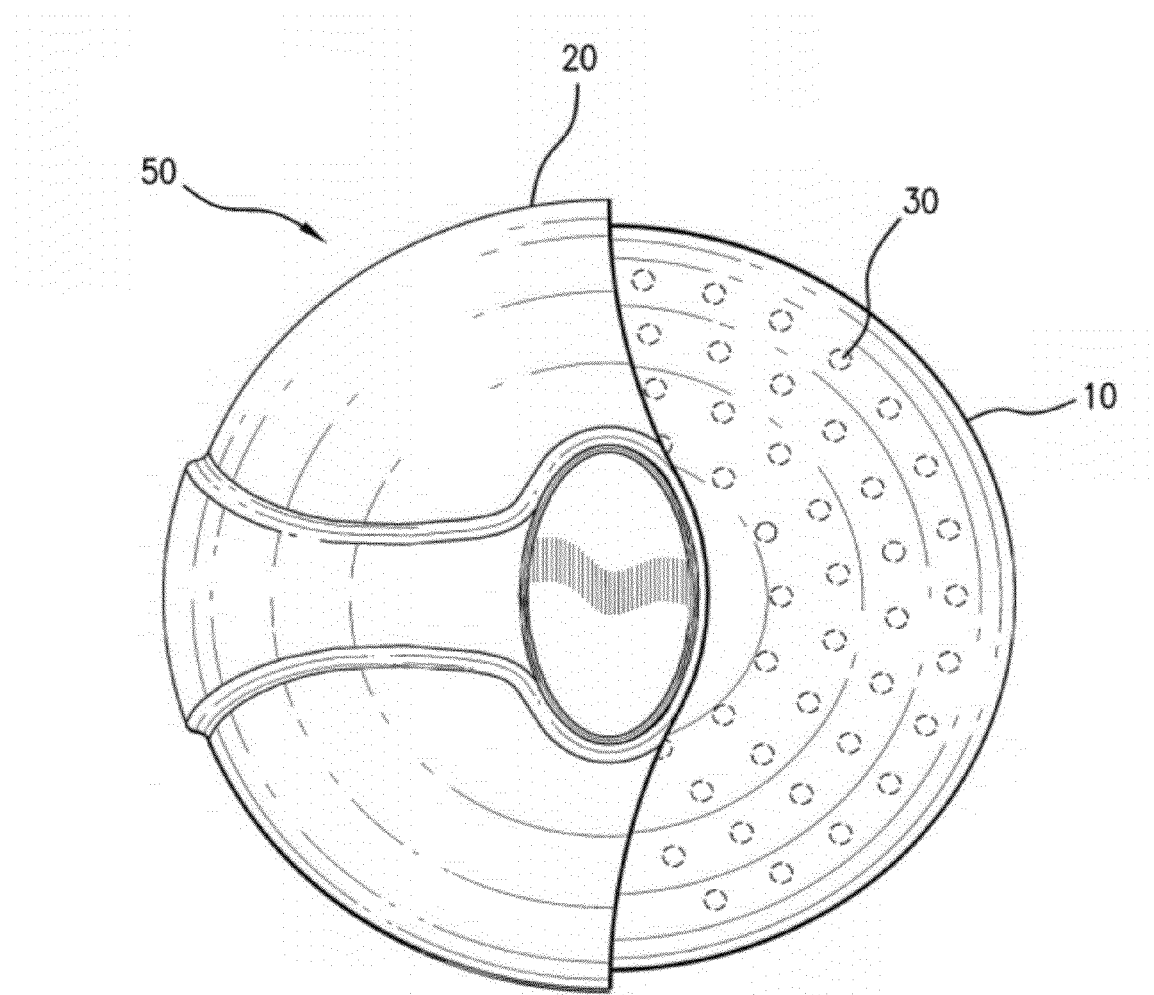
FIG. 3 is a top view of the example deodorizer according to an example embodiment of this invention, showing the holes of the housing in its open position.
Figure 4:
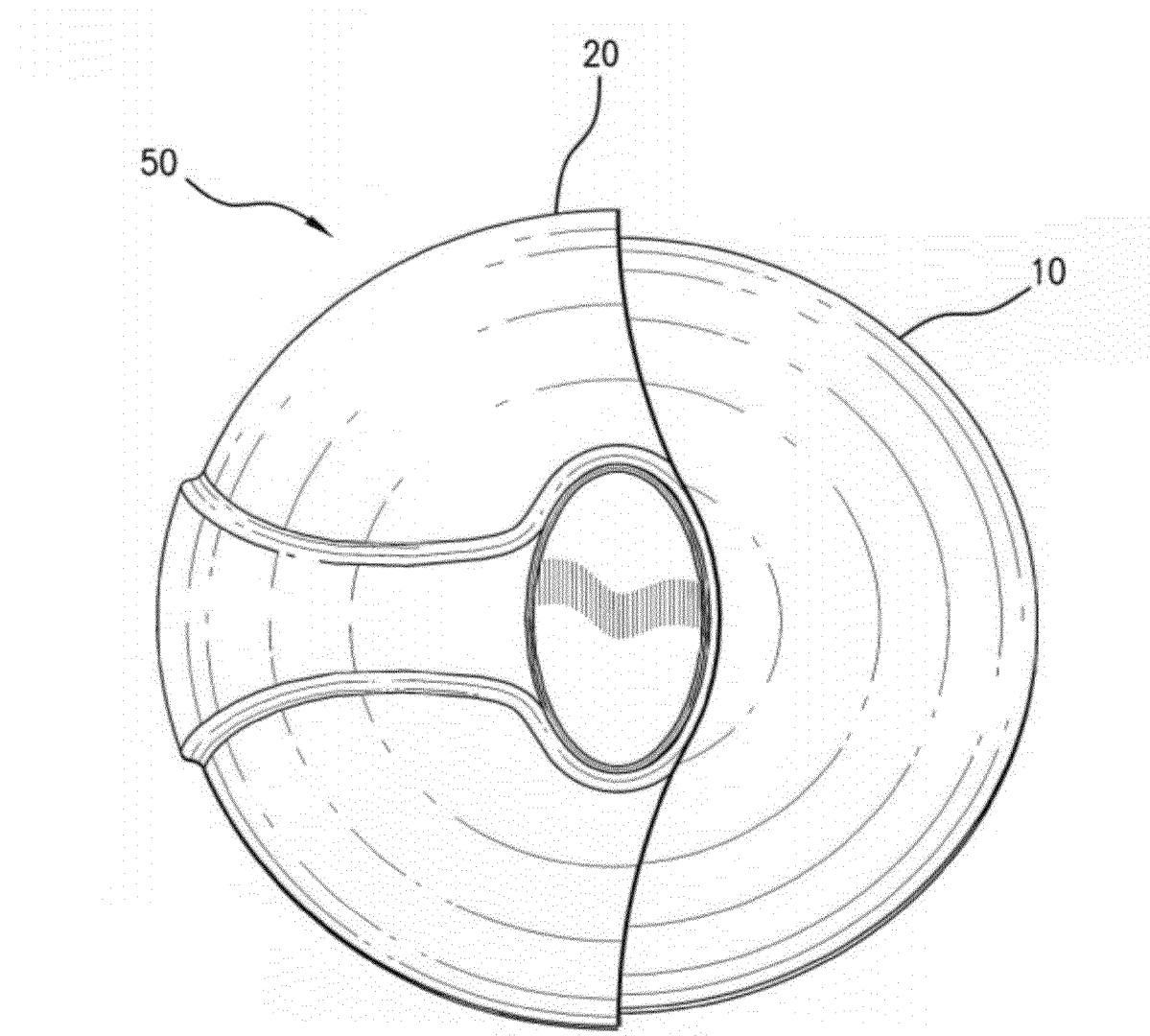
FIG. 4 is a top view of the example deodorizer according to an example embodiment of this invention, showing the holes of the housing in its closed position.

FIG. 1 is a prospective view of an example deodorizer, according to an example embodiment of the present invention. The example deodorizer 50 may include a housing 10 with a plurality of holes 30; and a sheath 20. FIG. 2 is a corresponding side view of FIG. 1. FIG. 3 and FIG. 4 are corresponding top views of FIG. 1 showing the holes 30 of the housing 10 in its open and closed positions, respectively.

The sheath 20 is movably connected to the housing 10, and movable from a closed position as shown in FIG. 4, to an open position as shown in FIG. 3. Alternatively, the sheath 20 may not be removable from the housing 10. The housing 10 and or sheath 20 may be molded from materials with minimal tendency to absorb the odor neutralizer and or fragrance. For example, the material of the housing 10 may be a plastic material, such as a talc filled, injection-moldable polypropylene material. The sheath 20 may be configured to retard the release of the odor neutralizing compositions into the environment though the holes 30 of the housing 10. As will be discussed in the example sections, it has been found that the flattened disc shape is particularly advantageous, providing improved performance while still allowing the device be conveniently inserted in a typical shoe.

Referring to FIGS. 1, 3, 4 and 6, the sheath 20 may be connected to the housing 10, for example, at the midpoint of the housing 10. In an alternatively way, more than one sheath may be connected to the housing 10. The sheath 20 and the housing 10, may also, for example, designed to allow for depiction of a trademark or symbol or a decoration pattern and the like.

Referring to FIGS. 1, 2, 3, and 5, the holes 30 are designed to control the vaporization rate of the odor neutralizing composition 60 in the carrier material 70. The number of the holes 30 is up to 50. Example embodiments of the housing 10 comprise 42 holes, or 30 holes, or 35 holes, or 25 holes, or 45 holes, etc.

The size of the holes 30 is up to 3.0 mm diameter. For example, the size of the holes 30 may be about 1.5 mm, or about 1.3 mm, etc. The number and size of the holes 30 may be varied to tune the example deodorizer so that it eliminates up to 90% of the malodor. For example, nearly 90% of a model shoe odor, isovaleric acid, is removed in 8 hours by a deodorizer 50 with the holes 30 fully open. The isovaleric acid test is known to those skilled in the art and is exemplified in U.S. Pat. No. 6,936,220. After each use, the holes 30 of the deodorizer 50 can be covered by the sheath 20 in a closed position. While not in use, the deodorizer 50 can be stored with the holes 30 in a closed position. The deodorizer 50 can be used for up to about 30 times.

Figure 7:
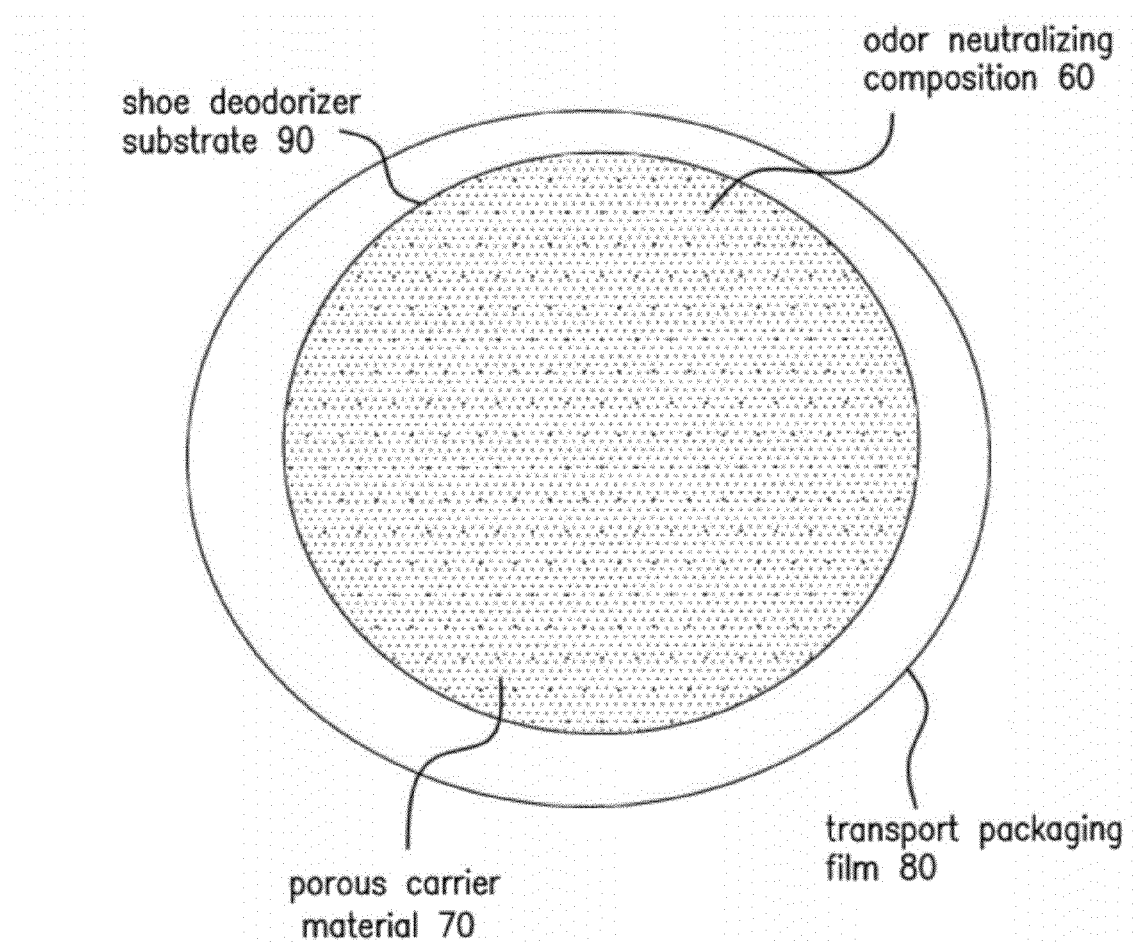
FIG. 7 is a view of another example deodorizer, according to an example embodiment of this invention.

One of the embodiments for an article of manufacture of the present invention, as shown in FIG. 7, comprises a shoe deodorize substrate 90 and a package 80. In FIG. 7, the shoe deodorizer substrate 90 comprises a porous carrier material 70 and an odor neutralizing composition 60. The porous carrier material 70 is formed in a monolithic form, e.g. a sphere or more preferably a flattened disk, without a casing and sized to insert in a shoe. The odor neutralizing composition 60 is in the porous carrier material 70. It will be appreciated that the example with a plastic housing, as shown in FIG. 16, could also be packaged in this manner.

The shoe deodorizer substrate 90 is protected against significant premature loss of odor neutralizing composition by heat sealing the deodorizer substrate 90 into a relatively thick, low organic vapor transport packaging film 80.

Preferably, the shoe deodorizer substrate 90 loses less than 5% of the odor neutralizing composition 60 under one month aging at 50° C., or under three months aging at 40° C. Preferably, the shoe deodorizer substrate 90 can be used for up to a year.

The example odor neutralizing composition 60 comprises undecylenic acid and/or a derivative thereof and or fragrances, and or flavor agents. Preferably, the amount of the undecylenic acid and or a derivative thereof is from about 5% to about 50% by weight of the odor neutralizing composition 60. Preferably, the undecylenic acid derivatives are methyl ester and ethyl ester undecylenic derivatives. More preferably, the undecylenic acid derivatives comprise a ratio of methyl ester undecylenic derivative to ethyl ester undecylenic derivative from about 5/95 to about 30/70 by weight.

In other example embodiments of the present invention, the amount and type of the odor neutralizer 60 varies to achieved a desired odor elimination and longevity of the formulation in a product. For example, 5 grams, or 2 grams, or 1.6 grams of odor neutralizer may be used in the shoe deodorizer substrate 90. It will be appreciated that it can be used alone or in combination with the device in FIGS. 1-6.

In one example embodiment of the present invention, the carrier material 70 is a porous polyalkylene material. Preferably, the carrier material 70 is polyethylene or microporous high density polyethylene (HDPE). Example embodiments of the carrier material 70 may contain an average pore diameter size to about 100 microns, or from about 45 microns to about 90 microns. The pore volume and internal pore surface area of the carrier material 70 in the preferred shoe deodorizer configuration allows for effective odor neutralization for up to thirty 8-hour (or overnight) shoe treatments.

The rate of release/vaporization of the odor neutralizing composition out of the carrier material is controlled by at least one of the following: a) the total amount of the porous carrier material and the amount of the odor neutralizing composition in the carrier material, b) the amount of relatively low volatility fragrance carrier in the composition, c) the average pore sizes pore tortuosity, and total pore internal surface area of the porous carrier material, d) the external surface area of the porous carrier material. The article of manufacture of a deodorizer substrate 90 in a package film 80, may have a shelf life of about one year to up to two years, upon appropriate tuning of the above variables.

Figure 8:
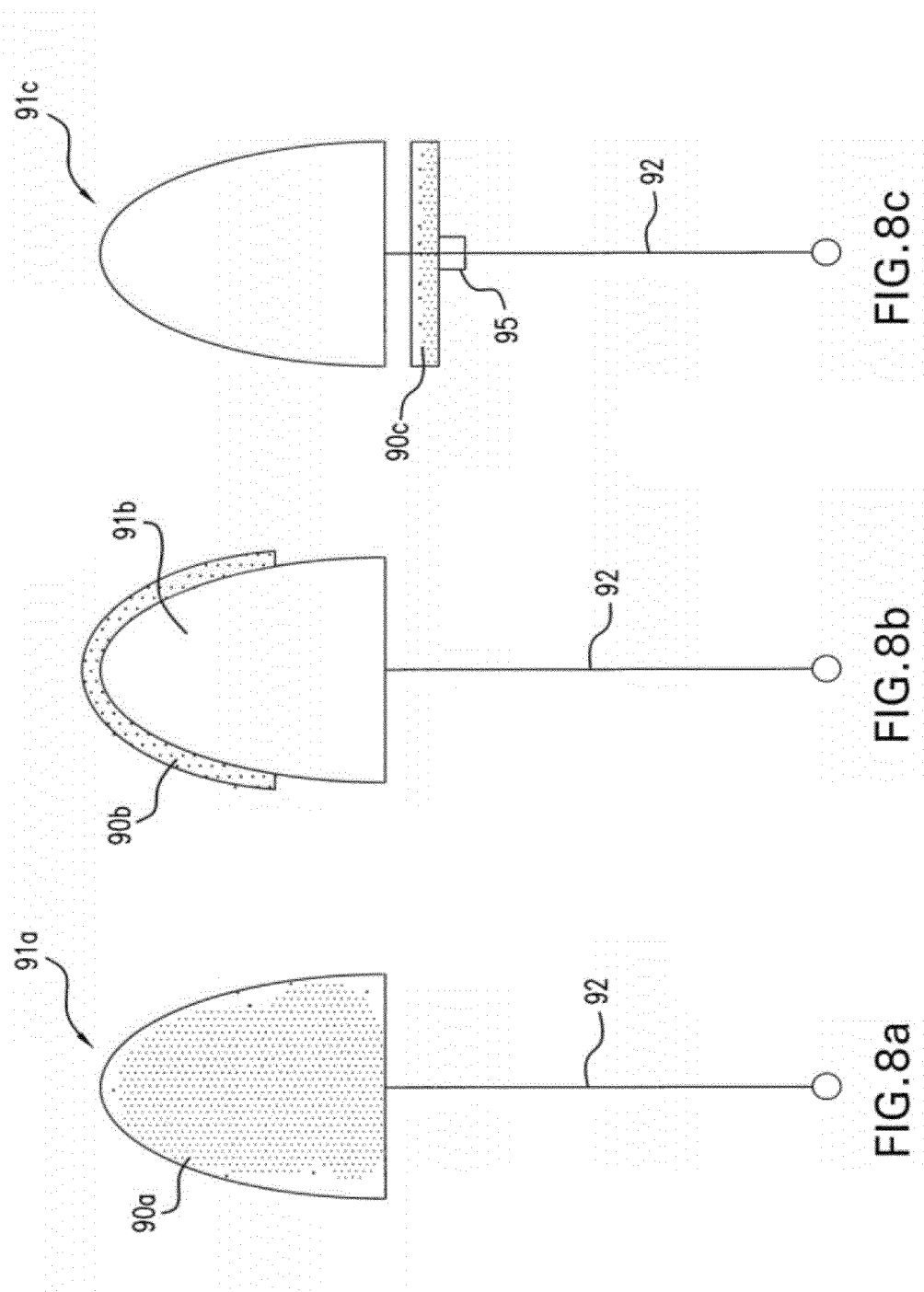
FIG. 8 is a set of views of an odor deodorizer substrate in different shapes.

The shoe deodorizer substrate 90 can be any shape, for example, a football, soccer ball, heart, flower, soap, triangle, cube, shell of a shoe tree, or disk. In one example embodiment, illustrated in FIG. 5a, a forefoot portion 91a of shoe tree can be essentially made entirely of shoe deodorizer substrate 90a, as shown in FIG. 8(a). The forefoot portion 91a can be attached to a mechanical part 92, such as a flexible rod, screw, or spring, which may be configured to hold the shoe tree in a shoe. In another example embodiment, illustrated in FIG. 5b, a shell in a shape of a shoe tree can be made of shoe deodorizer substrate 90b which be directly attached to the forefoot portion 91b of the shoe tree, e.g., using an adhesive, or with some other form of mechanical attachment such as a pin, hook and loop fabric, screw, etc. In yet another example embodiment of the present invention, illustrated in FIG. 5c, a disk shaped shoe deodorizer substrate 90 may be mechanically attached, e.g., using an adhesive, to a shoe tree forefoot portion 91c with a retainer 95, e.g., a nut or a washer assembly. The mechanical part 92, e.g., a spring or flexible rod, may pass through the substrate 90 to mechanically connect with the forefoot portion 91c, and may, in combination with the forefoot portion 91c, be configured to hold the shoe deodorizer in place in the shoe. Any of the above example deodorizers illustrated in FIG. 5a-c, may both eliminate shoe odor and keep the original shape of dress shoes at the same time.

In yet another example embodiment of the present invention, an example procedure for preparing an undecylenic acid and or an undecylenic acid derivative containing deodorizer substrate is provided. The example procedure may include
i) providing an odor neutralizing premix composition comprising an effective amount of an undecylenic acid and or an undecylenic acid derivative, fragrances and or flavors;
ii) forming a porous carrier material into a shape;
iii) applying the premix to the formed shaped carrier material; and
iv) allowing the release of an effective amount odor neutralizing composition from the carrier material.

Preferably, the premix is a liquid formulation. More preferably, the premix is applied into the formed shaped carrier material via absorption.

To more clearly describe the embodiments of the present invention, the following examples are provided. These examples are not intended to limit the scope of the invention, and one of skill in the art will understand that other embodiments are within the scope of the claims.

EXAMPLES

Example 1

Figure 13:
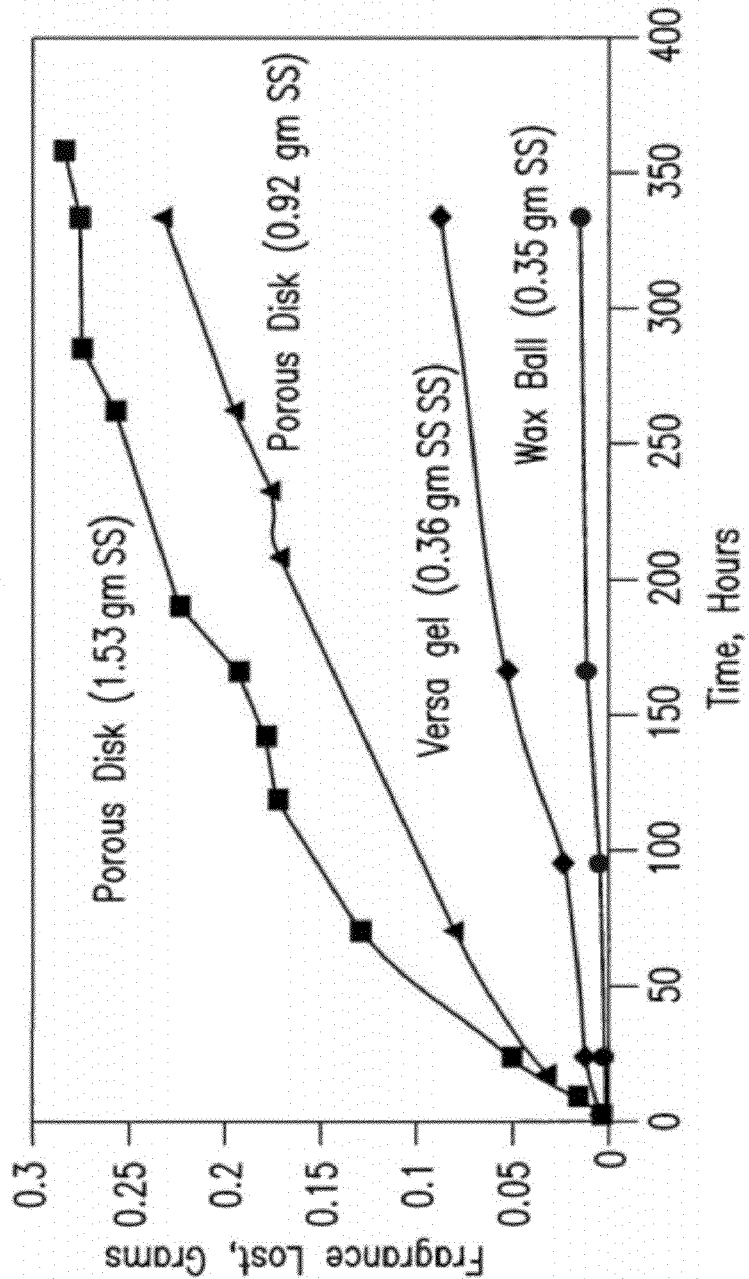
FIG. 13 is a graph depicting the results of experiments comparing three different fragrance/odor neutralizer carrier types: porous disk, versa gel and wax ball, that were evaluated for release rate of fragrance.

The Effect of the Carrier Type of the Deodorizer on the Diffusion of Odor Neutralizer from an Open Device As depicted in FIG. 13, three different fragrance/odor neutralizer "carrier types", porous disk, versa gel and wax ball, were evaluated for "release rate" of fragrance. The carriers are pre-loaded with specific amounts of the proprietary fragrance/odor neutralizer formulation. For the porous, high density, polyethylene disk carrier (supplied by INTECH Systems), the pre-loading is done immediately prior to starting the weight loss study by pipetting the formulation onto the disk while it sits in a molded plastic half sphere on the laboratory balance. The wax ball carrier was formulated and supplied by the fragrance/odor neutralizer manufacturer (Quest). The "Versagel" carrier (a proprietary polymer/mineral oil mixture) was formulated and supplied by the manufacturer of Versagel (Penreco). The "release rate" is measured as a weight loss, in grams, using a calibrated, four place, laboratory balance. These fragrance-loaded carriers were weighed at the times indicated in FIG. 13, which depicts how the rate of release of the fragrance/odor neutralizer formulation into the surrounding environment could be controlled by the selection of different carrier types, in addition to the amount of fragrance/odor neutralizer charged. FIG. 13 illustrates that the polyethylene disk carrier achieves more rapid fragrance/odor elimination diffusion that the gel or wax ball.

Example 2

Figure 9:
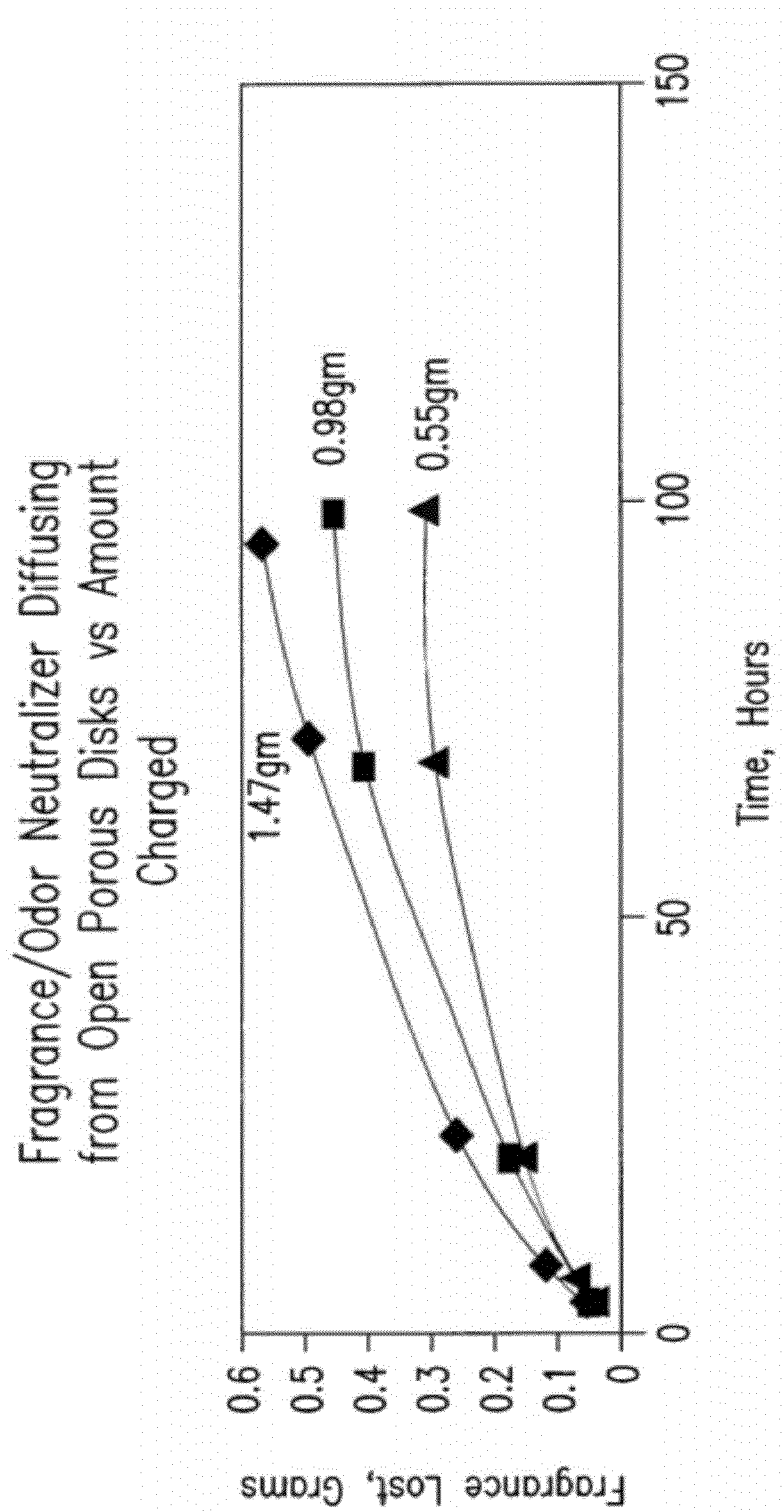
FIG. 9 is a graph depicting the results of experiments to determine the effect of the amount of fragrance/odor neutralizer charged to the preferred carrier type (a porous, high density polyethylene disk) on the release rate.

The Effect of the Amount Charged in the Deodorizer on the Rate of Diffusion of Odor Neutralizer from an Open Porous Disk As shown in FIG. 9, the effect of the amount of fragrance/odor neutralizer charged to the preferred carrier type (a porous, high density polyethylene disk) on the "release rate" was determined using the method described in Example 1. Three different sample amounts were added to the porous disk: 1.47 g, 0.98 g, and 0.55 g and the weight loss from the porous disks was followed for 100 hours. It was determined that higher loadings of fragrance had higher rates of loss. The weight loss from the porous disks was determined to be controlled by diffusion from the internal pores of the disk, followed by evaporation into the open environment.

Example 3

Figure 10:
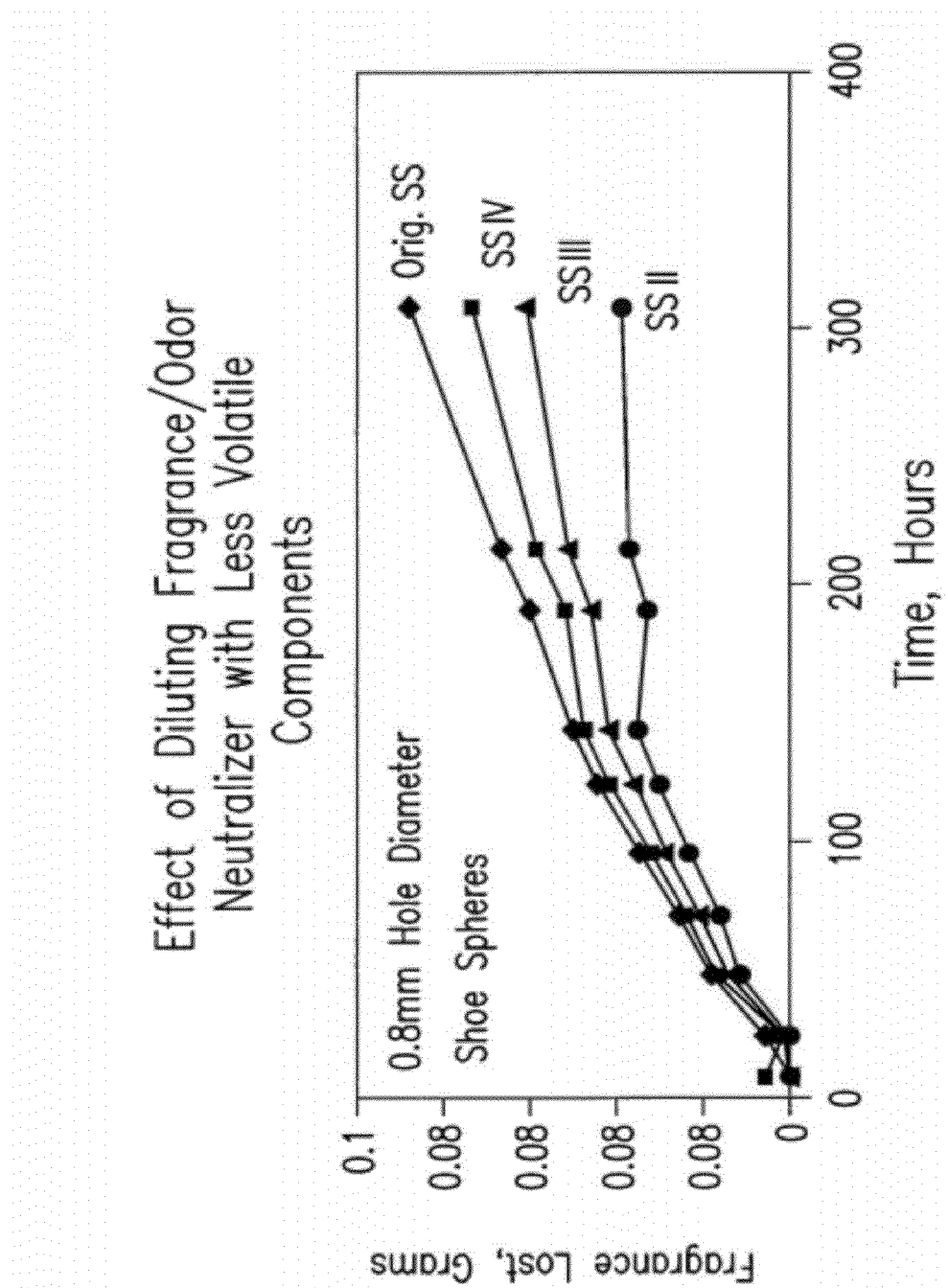
FIG. 10 is a graph depicting the results of experiments to determine how the release rate of the fragrance/odor neutralizer mixture can be modified and/or controlled via successive dilutions of an original, base formulation.

The Effect of Diluting Odor Neutralizer of the Deodorizer with Less Volatile Component on the Diffusion of Odor Neutralizer In the formulation of fragrance mixtures, dilution of the "high note", or more volatile components of a formulation, with either "lower note" and/or inert components is frequently done in order to reduce formulation costs, enhance the length of time the "higher notes" are released from the formulation, or to mute the olfactory perception to meet specific product requirements. FIG. 10 depicts how the "release rate" of the fragrance/odor neutralizer mixture can be modified/controlled via successive dilutions of an "original", base formulation. The formulations labeled SS IV, SS III and SS II, in that order, contained successively greater amounts of "low note" (i.e., less volatile) formulation components than the "base" formulation. These weight loss studies were carried out by loading a porous HDPE disk carrier with the same amount (ca. 1.5 gram) of each fragrance formulation as described in Examples 1 and 2 above. The loaded disks were placed into molded plastic assemblies as depicted in FIGS. 1-3, which consist of inner and outer rotatable housings. The outer housing of the assembly was rotated so as to expose an array of holes/openings formed in the inner housing, which allowed restricted escape of the fragrance/odor neutralizer into the surroundings. In this example, the holes measured about 0.8 mm in diameter. As shown in FIG. 10, SS II has lowest release rate—due to more "low note", less volatile formulation components.

Example 4

Figure 11:
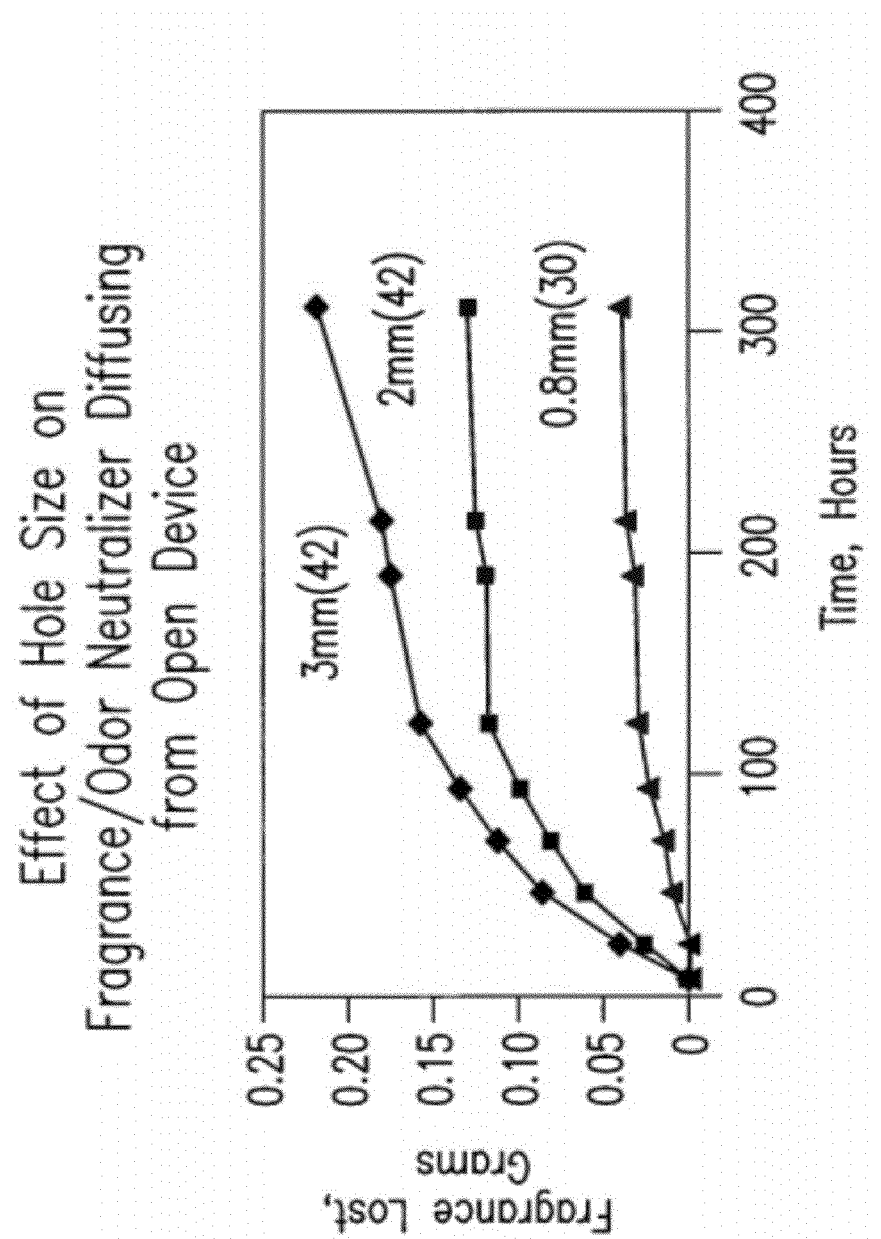
FIG. 11 is a graph depicting the results of experiments to determine the effect of the amount of open hole area in the inner, rotatable housing.

The Effect of the Size of the Holes in the Housing of the Deodorizer on the Diffusion of Odor Neutralizer from an Open Device FIG. 11 depicts the results of tests to determine the effect of the amount of open hole area in the inner rotatable housing. Three hole diameters were examined: ca.3 mm, ca.2 mm and ca.0.8 mm. The numbers in parentheses are the number of holes in the device. The device used was the molded plastic device described in Example 3 containing fragrance loaded on a porous HDPE disk carrier as described in Example 1. The fragrance used was SS II, which was loaded on a porous HDPE disk carrier as described in Examples 1 and 2 above. The smallest hole diameter (0.8 mm) presents the smallest open area for escape of the fragrance/odor neutralizer to diffuse out of the molded plastic assemblies. Selection of successively larger holes in the rotatable component of the assembly enables faster "release rates" into the surrounding environment to be achieved. After about 120 hours into the weight loss studies, the initial, fairly rapid "release rate" slows significantly, which may be due to the loss of the more volatile, "high notes" of the formulation mixture having diffused out of the plastic assembly.

Example 5

The effect of Open v. Closed Device on the Diffusion of Odor Neutralizer

Figure 5:
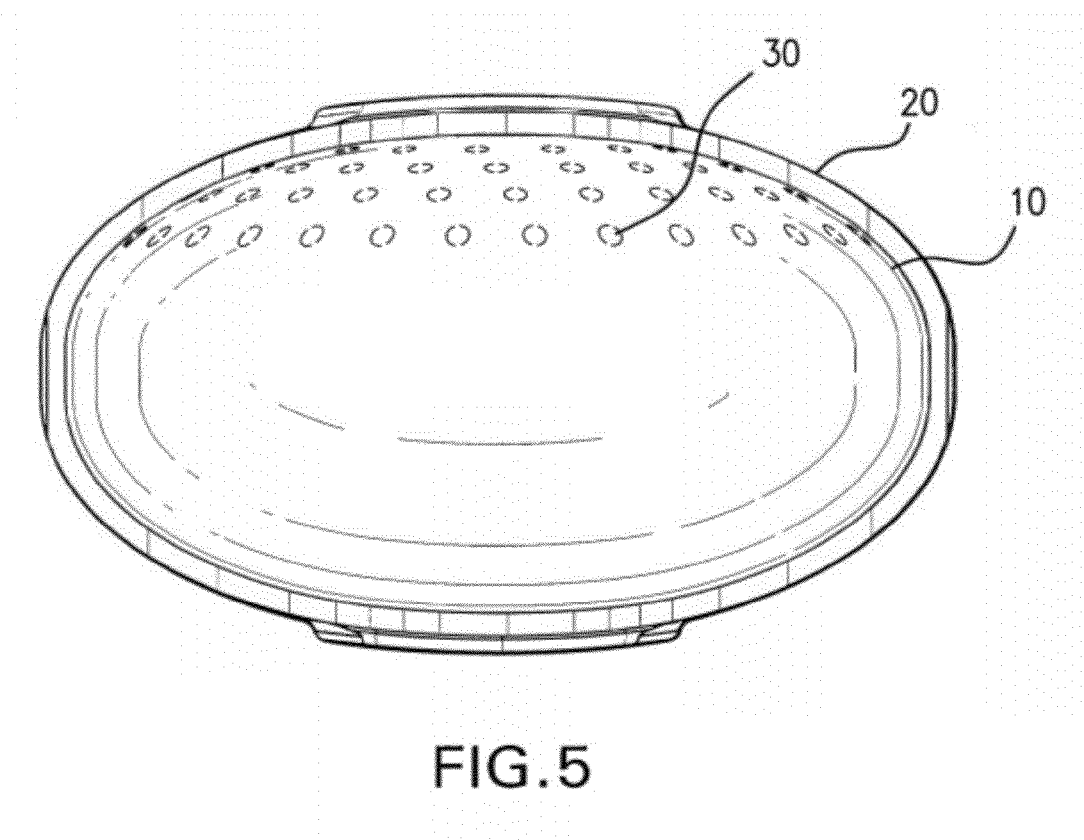
FIG. 5 is a front side view of the example deodorizer according to an example embodiment of this invention, showing the holes of the housing in its open position.
Figure 6:
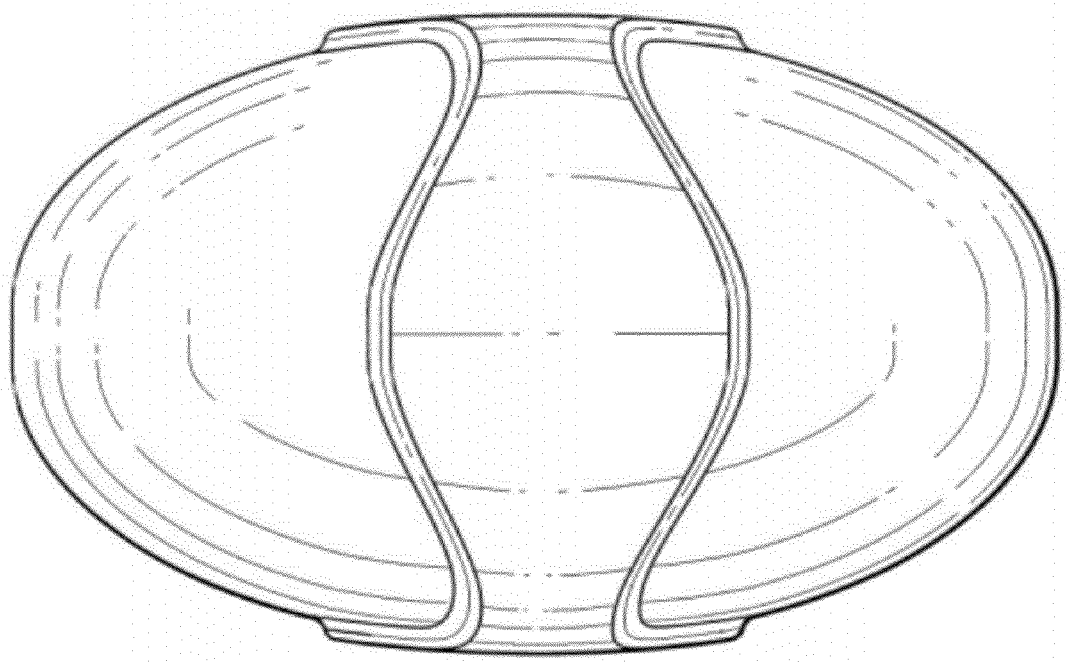
FIG. 6 is a back side view of the example deodorizer according to an example embodiment of this invention, showing the sheath connected to the housing.
Figure 12:
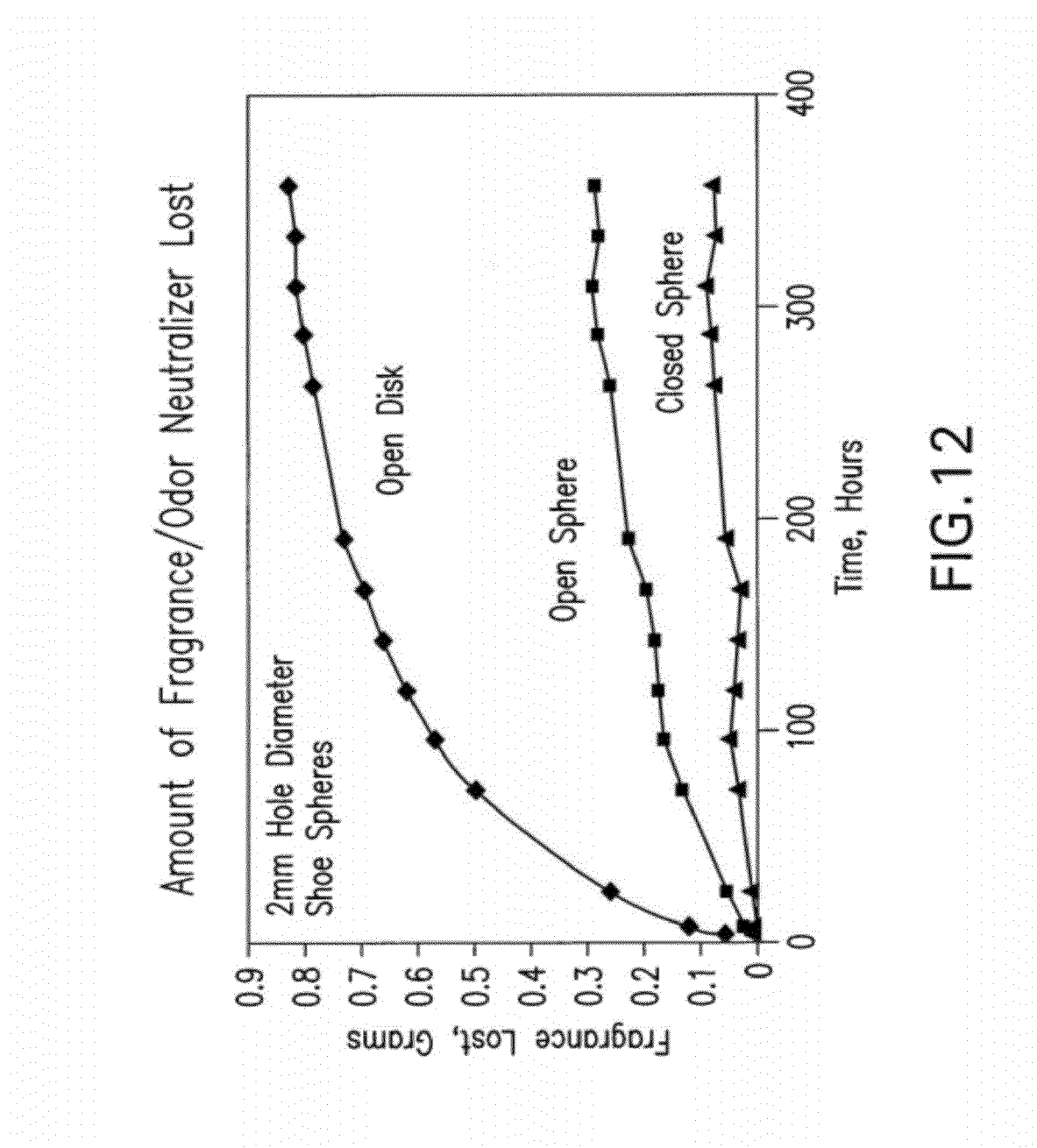
FIG. 12 is a graph depicting the results of experiments to determine the effect on the release rate of fragrance of the closing off of the assemblage of holes on the inner housing.

FIG. 12 depicts the effect on the "release rate" of fragrance of the closing off of the assemblage of holes on the inner housing by rotating the component until all the holes are covered by the outer housing. In the case of the "Open Sphere" and the "Closed Sphere", the device used was the molded plastic device described in Example 3 with forty two, 2 mm diameter holes in the rotatable, inner housing. The fragrance used was the base-formulation (Orig. SS), which was loaded on a porous HDPE disk carrier as described in Examples 1 and 2 above. For the tests on the disk within the device, the disk was loaded as it lay inside the assembled device. The "Open Disk" curve of FIG. 12 represents a control, where a fragrance loaded disk is not contained inside an assembled Shoe Sphere assembly, and demonstrates the significantly faster loss of fragrance. The "Closed Sphere" curve represents an assembled device as depicted in FIGS. 4-6 containing a loaded porous HDPE disk carrier inside with the holes on the inner housing completely covered by the outer housing of the device. The "Open Sphere" curve represents an assembled device as depicted in FIGS. 4-6 containing a loaded porous HDPE disk carrier inside with the holes on the inner housing fully exposed from the outer housing of the device. The weight loss study is pertinent in designing a device that would be re-useable for a selected number of applications for example "overnight applications"—provided that the assembled device was rotated into a closed position following completion of each use cycle. Thus the experiment demonstrates that when the device is not in use (i.e., holes are fully closed) the device releases fragrance at a relatively low rate compared to when in use with all holes fully exposed or when the disk carrier is completely exposed outside of a device.

In certain embodiments, appropriate packaging, such as a polyester film primary packaging and a vinyl or similar secondary packaging, would be used to establish shelf stability such as would be required during transportation, warehousing, and while awaiting sale in retail outlets. In certain embodiments, the primary packaging would allow for at least one year of storage prior to use. In certain embodiments, the primary packaging would allow for at least two years of storage prior to use. Shoe deodorizer devices, as described in Examples 3-5 and depicted in FIGS. 4-6, were tested for product life once out of the packaging and demonstrated up to 30 consecutive 8 hour "overnight" uses, using an "in-vitro" laboratory test from the fragrance/odor neutralizer supplier. In this test, unfragranced shoe insoles were treated with a "model" malodor substance, isovaleric acid in a distilled water salt solution. The insoles were equilibrated with the IVA in a closed container for 48 hours and then an "open" shoe deodorizer device was placed into a canvas "sneaker" shoe for 8 hours. During the 30 day testing period, the shoe deodorizer device was left "open" in the sneaker for 8 hours, following which it was closed off until the next sneaker treatment at the next selected time point. Headspace samples collected in a sampling tube placed over the sneaker/deodorizer device were then analyzed by GC-MS analysis for residual IVA. Percent reduction of IVA was calculated at preselected 8-hour application times by comparing the results to those of a "control" sneaker which did not contain a shoe deodorizer device. Initial studies in triplicate showed excellent reproducibility. Final studies were then done with single samples and a shoe deodorizer configuration with forty two, ca. 1.4 mm diameter holes and a slower releasing formulation (SS V).

The final preferred product configuration (with a plastic sphere containing forty two holes of ca. 1.4 mm diameter and with SS V formulation) packaged in a primary package of polyethylene terephthalate, and then in a secondary package of vinyl—was tested at 50° C. for a month and 40° C. for up to three months to assure "shelf stability". No expiration date is required for a product of this type.

Although the invention has been described with reference to particular preferred embodiments and examples, those skilled in the art will recognize that the scope of the invention is broader than those embodiments and examples contained herein.

What is claimed is:

1. An odor deodorizer, comprising:
   I) a disk-shaped, monolithic porous carrier material of microporous high density polyethylene, having pores in the range of 45-100 microns;
   ii) an odor neutralizing composition of undecylenic acid and/or a derivative thereof in the porous carrier material; and
   iii) a disk-shaped housing made of talc filled, injection-moldable polypropylene sized to fit in a shoe and having a plurality of holes and containing the porous carrier, the housing being movable between an open to a closed configuration.

2. An odor deodorizer comprising:
   i) a porous carrier material formed in a monolithic form;
   ii) an odor neutralizing composition in the porous carrier material; and
   iii) a housing containing a plurality of holes, the housing containing the porous carrier, wherein the material of the housing is a talc filled, injection-molded polypropylene material.

3. The odor deodorizer of claim 2 wherein the housing further comprises at least one sheath configured to cover at least a subset of the plurality of holes.

4. The odor deodorizer of claim 3 wherein the sheath is movably connected to the housing and movable from a closed position to an open position.

5. The odor deodorizer of claim 2 wherein the number of the holes is up to 50.

6. The odor deodorizer of claim 2 wherein the number of the holes is up to 42.

7. The odor deodorizer of claim 2 wherein the size of the holes is up to 3.0 mm in diameter.

8. The odor deodorizer of claim 2 wherein the size of the holes is up to 2.0 mm in diameter.

9. An article of manufacture, comprising:
   a shoe deodorizer substrate containing an effective amount of an undecylenic acid and or a derivative thereof in a porous monolithic carrier; and
   a sealed package formed at least in part of a heat sealing, low organic vapor transport packaging film, the package containing the shoe deodorizer substrate, wherein the sealed package further comprises a sealed inner layer of polyethylene terephthalate located inside the packaging film and surrounding the shoe deodorizer substrate.

* * * * *